US010858648B1

(12) United States Patent
Edgell

(10) Patent No.: US 10,858,648 B1
(45) Date of Patent: Dec. 8, 2020

(54) LABORATORY DIRECTED EVOLUTION VIA HG-SELECTION

(71) Applicant: Marshall Hall Edgell, Chapel Hill, NC (US)

(72) Inventor: Marshall Hall Edgell, Chapel Hill, NC (US)

( * ) Notice: Subject to any disclaimer, the term of this patent is extended or adjusted under 35 U.S.C. 154(b) by 0 days.

(21) Appl. No.: 16/247,019

(22) Filed: Jan. 14, 2019

Related U.S. Application Data

(60) Provisional application No. 62/616,667, filed on Jan. 12, 2018.

(51) Int. Cl.
*C40B 30/04* (2006.01)
*C12N 15/10* (2006.01)

(52) U.S. Cl.
CPC .......... *C12N 15/1024* (2013.01); *C40B 30/04* (2013.01)

(58) Field of Classification Search
None
See application file for complete search history.

(56) References Cited

U.S. PATENT DOCUMENTS

| 9,394,537 B2 | 7/2016 | Liu et al. |
| 2018/0187182 A1 | 7/2018 | Reintjes |

FOREIGN PATENT DOCUMENTS

WO 2012093128 A1 7/2012

OTHER PUBLICATIONS

Russel and Model (1986) JBC vol. 261 pp. 14997 to 15005.*
Joung et al., "A bacterial two-hybrid selection system for studying protein-dna and protein-protein interactions," PNAS, 2000, vol. 97, pp. 7382-7387.
Quimron et al., "Genomewide screens for *Escherichia coli* genes affecting growth of T7 bacteriophage," PNAS, 2006, vol. 103, pp. 19039-19044.
Maynard et al., "A forward-genetic screen and dynamic analysis of lambda phage host-dependencies revels an extensive interaction network and a new anti-viral strategy," PLos Genetics, 2010, vol. 6, pp. 1-15.

(Continued)

*Primary Examiner* — Christian C Boesen
(74) *Attorney, Agent, or Firm* — David M. Saravitz; Williams Mullen

(57) ABSTRACT

The present invention relates to methods and systems for the directed evolution of macromolecules. The methods comprise contacting a population of host cells with a population of infective viruses. The host cells contain a controlling gene encoding a controlling gene product that is required for replication of the infective viruses but is not required for the replication of the host cells. The infective viruses comprise a gene of interest encoding a protein to be evolved to contain a desired activity that is required for expression of the controlling gene. The controlling gene in the host cells is embedded in a genetic circuit such that the controlling gene product is only expressed when the gene of interest has evolved to encode an evolved protein comprising the desired activity that is required for expression of the controlling gene. The systems comprise the host cells and infective viruses, a controlling gene genetic circuit to link controlling gene product production with the desired activity and optionally, a lagoon, a cellstat and/or a suitable growth medium.

7 Claims, 7 Drawing Sheets

(56) References Cited

OTHER PUBLICATIONS

Na et al., "Synthetic inter-species cooperation of host and virus for targeted genetic evolution," J. Biotechnol., 2011, vol. 153, pp. 35-41.
Saluja et al., "Biochemical characterization of *Escherichia coli* temperature-sensitive dnaB mutants, dnaB522, dnaB70, dnaB43, and dnaB," J. Bact., 1995, vol. 177, pp. 1104-1111.
Ray et al., "Replication of Bacteriophage M13 IX. Requirement of the *Escherichia coli* dnaG function for M13 duplex DNA replication," J. Virology, 1975, vol. 16, pp. 348-355.
Gilchrist et al., "*Escherichia coli* rep gene: sequence of the gene, the encoded helicase, and its homology with uvrD," Nuc. Acids Res., 1987, vol. 15, pp. 465-475.
Esvelt et al., "A system for the continuous directed evolution of biomolecules," Nature, 2011, vol. 472, pp. 499-503.
Diggle et al., "Cooperation and conflict in quorum-sensing bacterial populations," Nature, 2007, vol. 450, pp. 411-415.
Kunkel et al., "Directed evolution to produce sludge communities with improved oxygen uptake abilities," Appl. Microbiol. Biotechnol., 2015, vol. 99, pp. 10725-10734.

* cited by examiner

LABORATORY DIRECTED EVOLUTION VIA HG-SELECTION

CROSS-REFERENCE TO RELATED APPLICATION

This application claims the benefit of U.S. Provisional Patent Application No. 62/616,667, filed Jan. 12, 2018, which is hereby incorporated herein in its entirety by reference.

FIELD OF THE INVENTION

The present invention relates to the field of directed evolution of nucleic acids and the gene products encoded thereby.

BACKGROUND OF THE INVENTION

Continuous evolution of genes in viruses such as bacteriophages has the potential to become a potent protein engineering tool. In this process, the continuous evolution of a microorganism rapidly produces a protein-encoding DNA sequence which has undergone many generations of mutation and selection for a particular property of said protein (for example, binding to a target protein or target DNA sequence). The generality of this approach to protein engineering is limited only by the ability to insert an expressible initial gene into the replicating micro-organism and create a selection mechanism for the desired activity. This invention provides a design to provide those features.

Currently the best-practice in directed evolution exploits the rapid reproduction of filamentous bacteriophages (bacterial viruses) to evolve novel proteins. A transformed *Escherichia coli* (*E. coli*) host cell provides a high level of mutation as well as a fitness selection mechanism that rewards virus genomes encoding the desired property. As in natural evolution, directed evolution requires repeated cycles of the following three processes: (1) variation, or mutations, to allow for new or enhanced functionality; (2) selection that gives individuals with the desired new or enhanced functionality a reproductive advantage over individuals that exhibit a lesser degree of said functionality; and (3) reproduction to pass the selected functionality to the next generation.

Current continuous evolution procedures can induce elevated mutation rates with external agents or via plasmids bearing genes that enhance the mutation rate, in order to rapidly sample a large portion of the evolutionary landscape. These elevated mutation rates must be avoided during the cultivation of the host cells and may be induced by an external agent when the host cells have been transferred to an environment where they are subject to infection by the evolving virus. As a result, both the replicating host cell and the infective viruses being produced may contain a large number of mutations.

Engineering novel proteins via continuous evolution of viral borne genes currently requires the host to be transformed with two additional functions: (1) a mutagenesis vector that provides an elevated rate of viral mutation, and (2) a selection mechanism that gives a reproductive advantage to the genotype encoding the product producing the desired activity.

BRIEF SUMMARY OF THE INVENTION

This present invention is drawn to continuous evolution methods and systems which collectively referred to herein as HG-Selection (Host Gene Selection). The continuous evolution methods of the present invention comprise growing host cells and infective viruses comprising a gene that is intended to evolve to produce a desired activity. The desired activity can be, for example, the ability to bind to a desired target that is a protein or specific DNA sequence. The host cell comprises a host gene encoding a host gene product. The host gene and host gene product are referred to herein as the controlling gene and controlling gene product, respectively. The controlling gene product is not required for host cell replication. However, the controlling gene product either is required for the reproduction of the virus in the host cell, or at least enhances the reproduction of the virus in the host cell comprising the controlling gene product, when compared to a host cell lacking the controlling gene product. The host cell can further comprises a genetic circuit capable of causing the expression of a wild-type version of the controlling gene product in the host cell in the presence of the desired activity. Thus, the reproduction of viruses comprising a gene that has evolved to produce a gene product (or evolving protein) that has the desired activity is increased, thereby "rewarding" the genotype of this viral gene by increasing the number of phages carrying that genotype.

Any virus/host cell/host gene combination can be used in the methods and systems of the present invention if the controlling gene product encoded by the controlling gene is needed for virus replication but not for host cell replication. For example, the methods of the present invention can comprise the use of the bacteriophage T7 growing in host cells mutant for trxA, cmk, gmhB, or galU (Qimron et al. 2006), or lambda bacteriophage growing in host cells mutant for hflC, hflD, hflK, nusB, dnaJ, manZ, ihfA, ihfB, lamB, malI, cyaA, ybeD, yecR, or yneJ (Maynard et al., 2010) or bacteriophage M13 growing on host cells mutant for trxA (Russel and Model), dnaA, dnaB (Saluja and Godson), dnaC, dnaG (Ray et al.), dnaE, or rep (Gilchrist and Denhardt). However, the present invention is not limited to bacterial cells and viruses that can infect and reproduce in bacterial cells (i.e. bacteriophages). Any combination of a prokaryotic or eukaryotic host cell and a virus capable of infecting and reproducing within the host cell when the controlling gene is expressed can be used in the methods of the present invention.

The methods can further comprise use of a host cell cultivation system supplying uninfected host cells to a vessel containing a population of evolving viruses. The infecting virus contains a complete wild-type virus genome plus a gene for the protein to be evolved that is fused to an RNA polymerase. Mutagenesis can be induced in the host cells, either globally or as a response to infection. The host cell comprises the controlling gene integrated into its genome or on a plasmid. The selection mechanism involves expression in the host cell of the controlling gene in response to the presence in the host cells of the desired activity of the evolving protein, whereby the controlling gene product (i.e. a protein) is produced in the host cell. An individual virus in the population comprising a DNA sequence encoding a protein (i.e. the evolving protein) comprising the desired activity (e.g. the potential ligand protein binding to the target protein or DNA sequence) will be "rewarded" through the expression of the controlling gene in the host, resulting increased reproduction of progeny viruses with a genotype identical to that individual virus. Viruses encoding an evolving protein which does not exhibit the desired activity will not be able to replicate.

DETAILED DESCRIPTION OF THE INVENTION

Figure 1:
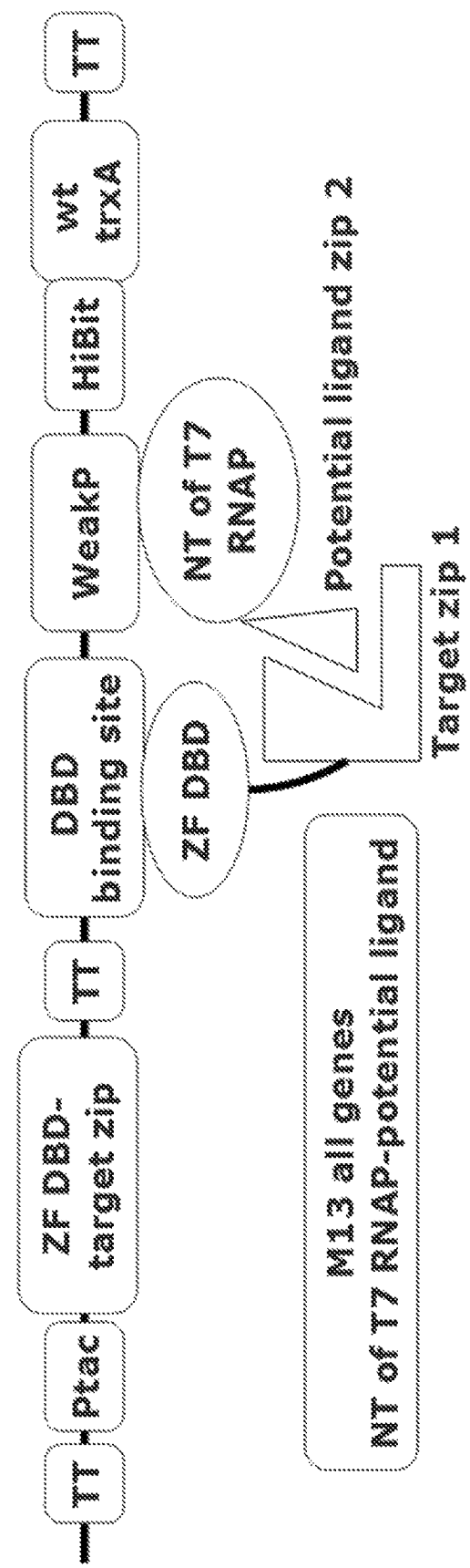
FIG. 1 is a general schematic of an embodiment of the HG-Selection method using the *E. coli* gene, trxA, as an example for the controlling gene and is a method for evolving protein ligands that bind to a desired target protein. The desired activity is for the potential ligand to evolve to recognize a target with enough affinity to promote expression of wild-type trxA. This occurs when the RNA Polymerase (RNAP) is brought to the vicinity of the promoter driving trxA transcription via binding to the target protein which is held in the vicinity of the promoter by the zinc-finger (ZF) DNA binding protein (Joung et al.). The host contains a mutant, trxJW5856-2 where the wild-type trxA gene has been inactivated by a point mutation. The infective virus (e.g. M13) cannot replicate without the trxA protein produced by the *E. coli* controlling gene (in this example, trxA). If mutagenesis allows enough binding of the potential ligand to the target that would give rise to some transcription and some production of a HiBit peptide-wild-type trxA fusion protein that M13 needs to replicate and propagate the mutated version of the potential ligand. TT represents a transcription terminator that blocks transcription from upstream, Ptac is a promoter controlled by the amount of inducer (IPTG) in the medium, ZF DBD is a strong zinc finger binding protein that recognizes and binds to the DBD DNA binding site, wealP is a weak promoter to which the T7 RNAP will bind and intiate transcription, HiBit is a small peptide (Promega Corporation, Madison, Wis.) that gives a very strong luminescence signal when exposed to the appropriate assay solution, zip and zip1 is the example leucine zipper target, zip 2 is the example leucine zipper ligand, NT is the n-terminal module of the T7 RNA polymerase.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

DEFINITIONS

In the context of this disclosure, a number of terms and abbreviations are used. The following definitions are provided.

Desired Activity: A desired activity is a property of the evolving protein that is intended to be enhanced. For example, the desired activity can be the ability to bind with another protein which is designated as the target or the ability to bind to a desired DNA sequence designated as the target.

Target: A target is a protein or a DNA substrate of interest to which the protein to be evolved using the methods of the present invention is intended to bind. The target is produced by the host organism and not subjected to evolutionary pressure.

Controlling gene: A controlling gene is a gene in the viral host genome that: is required for infective virus replication but not required for host cell replication; and has been mutated to be inactive in the host. In one embodiment of the invention that is described hereinbelow, the controlling gene is trxA.

Genotype: A genotype is the particular functionality of each of the genes in an organism.

Plasmid: A plasmid is an autonomously replicating circular DNA in the host.

Host: A host is a virus sensitive organism or cell transformed with plasmids bearing various genetic circuits to affect the reproduction of the evolving gene based upon a desired activity exhibited by the evolving protein. The host organism should not be subject to evolutionary pressure. In some embodiments of the invention, the host is a cell (i.e. a "host cell") such as, for example, bacterial cell. In certain embodiments of the invention, the host, or cell thereof, or the host cell is suitable or competent for infection by, and replication and packaging of, an infective virus of interest.

Infective Virus: An infective virus is a virus carrying the gene to be evolved and dependent on the controlling gene either for full or partial replication. In one embodiment of the invention that is described hereinbelow, the infective virus is a filamentous bacteriophage.

Phage: The term "phage" as used herein is intended to mean "bacteriophage", unless stated otherwise or a different meaning is apparent from the context of usage.

Selection mechanism: A selection mechanism is a process by which a particular desired activity results in increased reproduction of the entity encoding the genes associated with that activity. For example, a protein gene carried by a virus is selected based on how well it's protein binds to a second protein but is itself not subjected to evolutionary pressure.

Cellstat: A cellstat is a vessel in which the host cells are propagated prior to infection by an evolving virus. The cellstat environment is designed to maintain low levels of mutagenesis and avoid selective pressure on the host cells.

Lagoon: A lagoon is a vessel in which host cells come into contact with and can be infected by an evolving virus and where subsequent generations of competing viral particles are maintained. The lagoon environment is designed to enhance mutagenesis in order to accelerate virus evolution.

Messenger RNA (mRNA): A messenger RNA is a nucleic acid molecule that is used by a ribosome as a template for the production of a protein via translation.

Promoter. A promoter is a sequence that RNA polymerase binds to start transcription.

RNA Polymerase: RNA polymerase is an enzyme that can use a gene as a template to produce an RNA in a process known as transcription. When the gene encodes a protein, RNA polymerase can produce an mRNA or pre-mRNA. It is recognized that a pre-mRNA comprises one or more exons and one or more introns and that the introns can be spliced out by a host cell, particularly a eukaryotic host cell, after transcription to produce an mRNA, which does not contain introns.

DESCRIPTION

The present invention is drawn to method and systems for the continuous, directed evolution of macromolecules, particularly proteins and nucleic acid molecules encoding such proteins. The methods and systems of the present invention find use in making new forms of such macromolecules including, for example, proteins that comprise a desired activity that the protein did not have prior to being subjected to the methods and systems of the present invention. For example, the methods and systems of the present invention can be used to make proteins that bind to, or otherwise recognize, a specific DNA or RNA sequence of interest or that bind to, or otherwise recognize, a specific protein of interest or even to a domain or other part of such a protein of interest.

The methods of directed evolution of macromolecules of the present invention comprise contacting a population of host cells in a culture medium with a population of infective viruses. Any combination of host cells and viruses that are capable of infecting and reproducing in the host cells can be employed in the methods of the present invention including both prokaryotic and eukaryotic host cells and viruses capable of infecting and reproducing in such prokaryotic host cells and eukaryotic host cells, respectively. In one embodiment of the invention that is described in detail below, the host cells are *Escherichia coli* (*E. coli*) and the infective viruses are M13 bacteriophages.

The host cells and infective viruses can be grown in any culture medium that allows for the growth and replication of both the host cells and the infective viruses. Likewise, the host cells and infective viruses can be grown under environmental conditions that support the growth and replication of both the host cells and the infective viruses. Suitable culture media and environment conditions are known in the art for numerous host cells and infective viruses that can be used in the methods and systems of the present invention. See generally Molecular Cloning., M. Green and J. Sambrock, Cold Spring Harbor Laboratory Press, (2012). It is recognized that the selection of a suitable culture medium and a suitable culture medium can depend the particular combination of host cell and virus used in an embodiment of the present invention.

The host cells of the present invention comprise a controlling gene the encodes a controlling gene product that is produced by the host cells under certain conditions. The controlling gene product is either required for replication or at least enhances the replication of the infective viruses when the controlling gene product is present in the host cells, relative to the replication of the infective viruses when the controlling gene product is not present in the host cells. The controlling gene is, however, not required for the replication of the host cells.

The methods for making a protein ligand (i.e. a protein of interest) to target a protein or a target nucleic acid sequence involves infective viruses comprising a complete wild-type virus genome and a gene of interest encoding a fusion protein comprising a protein of interest operably linked to an RNA polymerase. The protein of interest is desired to be evolved or otherwise modified to comprise a desired activity, wherein the controlling gene is only capable of expressing the controlling gene product in the host cells in the presence of the desired activity. The protein of interest can be, for example, any naturally occurring or artificial (i.e. synthetic) protein or can be one or more domains or parts of any such naturally occurring or artificial protein. While the fusion protein is typically comprised of a protein of interest and RNA polymerase, it is recognized that a fusion protein of the present invention also encompasses, for example, naturally occurring proteins comprising both a domain or portion that is capable of evolving to the desired activity and a domain or portion comprising RNA polymerase activity. Preferably, for such a protein, the domain or portion that is capable of evolving to the desired activity can be separated from a domain or portion comprising RNA polymerase activity without loss or a significant reduction in the respective activities of those domains or portions. An example of a protein comprising both a domain or portion that is capable of evolving to the desired activity and a domain or portion comprising RNA polymerase activity is T7 RNA polymerase. Use of T7 RNA polymerase as the fusion protein in an embodiment of the present invention is further described below.

The RNA polymerase in the fusion protein can be any RNA polymerase protein or part or domain thereof that comprises RNA polymerase activity in the host cells and is capable of transcribing the controlling gene in the presence of the desired activity. Preferably, the RNA polymerase is not capable of transcribing the controlling gene in the cell unless the desired activity is also present in the host cell. It is recognized, however, that some very limited transcription of the controlling gene by the RNA polymerase might occur in the host cells when the desired activity is not present in the host cells. It is believed that such limited transcription of the controlling gene by the RNA polymerase in the host cells when the desired activity is not present in the host cells will not have a detrimental impact on the methods of the present invention.

The methods of the present invention further comprise incubating the populations of host cells and infective viruses under conditions allowing for the mutation of the gene of interest and replication of infective viruses comprising an evolved gene of interest that encodes a fusion protein comprising the desired activity. While mutations naturally occur in genes, it is often desirable to enhance the mutation rate in methods of directed evolution by exposing the infective viruses to mutagenic conditions. In some embodiments of the invention, infective viruses are exposed to mutagenic conditions before contacting the host cells. In other embodiments, the infective viruses are exposed to mutagenic conditions while in contact with the host cells. In yet other embodiments, the infective viruses are exposed to mutagenic conditions before contacting the host cells and also exposed to the same or different mutagenic conditions while in contact with the host cells. The mutagenic conditions can be applied to the infective viruses while in contact with the host cells for a limited duration, repeated periodically, or continuously depending on a number of facts such as, for example, the type of mutagenesis applied (i.e. biological, chemical, physical) desired level of mutagenesis, the incubation conditions, the type of infective virus, the type of host cell, and the like.

Methods for mutagenizing viruses, cells, and organisms are generally known in the art and involve exposing the viruses, cells, and organisms to mutagenic conditions for a period of time that can vary depending on, for example, the desired level of mutagenesis, the incubation conditions, and the type of virus, cell. Such mutagenic conditions can be, for example, biological, chemical, or physical in nature. Mutagenic conditions that are biological in nature include, but are not limited to, the use of the MP6 plasmid in *E. coli* cells to enhance the mutagenesis rate. In an embodiment of the invention that is described below, *E. coli* host cells comprise the MP6 plasmid which is known to enhance significantly the mutagenesis rate of the host cells comprising MP6 plasmid and of infective viruses, relative to the mutagenesis rate in cells lacking the MP6 plasmid and of infective viruses.

Mutagenic conditions that are chemical or physical in nature involve exposing the virus, cell, or organism to a chemical mutagen or physical mutagen, respectively. Chemical mutagens, include, but are not limited to, ethyl methanesulfonate (EMS), base analogues (e.g., 5-bromouracil), related compounds (e.g., 8-ethoxy caffeine), antibiotics (e.g., streptonigrin), alkylating agents (e.g., sulfur mustards, nitrogen mustards, epoxides, ethylenamines, sulfates, sulfonates, sulfones, lactones), azide, hydroxylamine, nitrous acid, or acridines. Physical mutagens, include, but are not limited to, X-rays, Gamma rays (e.g., cobalt 60 or cesium 137), neutrons, (e.g., product of nuclear fission by uranium 235 in an atomic reactor), Beta radiation (e.g., emitted from radioisotopes such as phosphorus 32 or carbon 14), and ultraviolet radiation.

In the methods of the present invention, the host cells and infective viruses are incubated together for a period of time. In general, the period of time will depend on how long it takes for the gene of interest to evolve into an evolved gene of interest that encodes a fusion protein comprising the desired activity. Those of skill in the art know and understand that such a period of time will vary pending on a number of factors including, for example, the protein of interest, the desired activity, the type of infective virus, the type of host cell, the mutagenesis rate, the mutagenic condition, the frequency and duration of the exposing the infective viruses to the mutagenic conditions, and the incubation conditions. In many embodiments of the methods of the present invention, the period of time is at least 1, 2, 3, 4, 5, 6, 7, 8, 9, 10, 11, 12, 13, 14, 15, 20, 25, 30, 40, or 50 days.

During the period of time when the populations of host cells and infective viruses are incubated together in a culture medium, it can be advantageous in certain embodiments of the invention to remove a portion of the infective viruses and host cells from the culture medium and replaced with fresh host cells. In embodiments of the invention involving the use of a liquid culture medium, a portion of the culture medium can be withdrawn and replaced with an equal portion of fresh culture medium comprising the fresh host cells. The amount of culture medium removed and the amount of fresh culture medium and the density of fresh host cells therein will be empirically determined depending a number of factors such as, for example, the type of host cells and/or infective viruses, the host cell and/or virus density in the culture medium at the time of removal, and the particular culture medium. In some embodiments, the amount of culture medium that is removed will be at least about 10%, 20%, 30%, 40%, 50%, or 75% of the total volume of the culture medium in which the infective viruses and host cells are being incubated and replaced with about the same volume of fresh culture medium containing fresh host cells.

If desired, the removal of culture medium comprising the host cells and infective viruses and the subsequent replacement of the removed culture medium with fresh culture medium containing fresh host cells can be done one or more time during or at a specified frequency such as, for example, every 10, 20, 30, 40, 50, 60 minutes or more depending on, for example, the growth rate of the host cells and/or infective viruses. In embodiments involving the removal of the culture medium and its replacement with fresh culture medium containing fresh host cells are at a specified frequency (e.g. every 30 minutes), it is recognized that it can be advantageous to use automated systems for such frequent replacement and removal. Moreover, it is recognized that methods of the present invention can be readily adapted to an automated format that requires a lesser involvement of laboratory workers that are using non-automated laboratory equipment and/or instruments.

The host cells of the present invention comprise a controlling gene encoding a controlling gene product that is required for replication, or enhances the replication of the infective viruses, but is not required for the replication of the host cells. While the controlling gene can be located in the genome of the host cell, the controlling gene is preferably on a plasmid that is introduced into the host cells. Using standard molecular biology techniques, a controlling gene can be introduced into a plasmid and then introduced into the host cells. In embodiments of the invention in which the controlling gene is located in the host genome, a controlling gene can be introduced into the genome of the host cells or an existing gene in the genome of the host cell can be converted to a controlling gene by, for example, modifying or engineering the DNA sequence of a portion (e.g. promoter region) of the existing gene in such a manner through the use of genome editing technologies that it is not capable of being expressed in the host cells unless the desired activity is also present.

It is noted that the methods and systems of the present invention are suitable for use with the two-hybrid system disclosed in (Joung et al.) and as described. However, any two-hybrid system that can be used for expression of the controlling gene can be used with the methods and systems of the present invention.

An example of an embodiment of the present invention using a two-hybrid system is shown in FIG. 1. In such a two-hybrid system, the desired activity is binding to a target protein. The target protein is operably linked to a DNA-binding domain (DBD) that is capable of binding to a specific DNA sequence of interest (DBD binding site) that is in vicinity of the controlling gene, particularly in the vicinity of the promoter for the controlling gene. Preferably, the promoter for the controlling gene is a weak promoter (WeakP). The protein of interest is a protein ligand to be evolved to comprise the desired activity of binding to the target protein. The protein of interest is fused to an RNA polymerase that is not capable of transcribing the controlling gene unless the RNA polymerase is in the vicinity of the weak promoter. Once the protein of interest has evolved to comprise the desired activity, the fusion protein comprising it (i.e. the evolved protein-RNA polymerase fusion protein) can be bind to the protein target-DBD fusion protein which is bound, or then binds, to the DBD binding site near the weak promoter, whereby the RNA polymerase portion of the evolved protein-RNA polymerase fusion protein transcribes the controlling gene.

While the example shown in FIG. 1 indicates that the DBD is a DBD from a zinc finger (ZF) protein, the methods and systems of the present invention do not depend on particularly type of DBD. Any DBD know in the art can be used in the methods and systems of the present invention including, but not limited to, ZF DBDs and DBDs from transcription-activator-like (TAL) effector proteins. Both the ZF and TAL DBDs can be engineered to bind a DNA sequence of interest. See, for example, Choo et al. (1994) Nature 372:645; Pomerantz et al., (1995) Science 267:93-96; Liu et al., PNAS 94:5525-5530 (1997); Guan et al. (2002) PNAS 99:13296-13301, and U.S. Pat. No. 8,420,782.

The methods of directed evolution of macromolecules of the present invention allow for the production of an evolved gene of interest that encodes a protein comprising the desired activity. The evolved gene of interest can be isolated from the infective viruses and, if desired, also sequenced using standard molecular biology methods that are known in the art or described elsewhere herein. Typically, the portion of the evolved gene of interest corresponding to the protein of interest is separated from the remaining portion(s) of the evolved gene of interest to yield a gene encoding an evolved protein comprising the desired activity. Alternately, a nucleic molecule comprising the gene encoding the evolved protein can be synthesized using standard techniques known in the art such as, for example, chemical DNA synthesis.

The evolved protein can be produced, if desired, by expressing the gene encoding the evolved protein in a cell or organism and then isolating the evolved protein from the cell or organism using standard protein expression and isolation methods. Alternatively, the evolved protein can be chemically synthesized using standard chemical protein synthesis methods.

Thus, the present invention provides isolated evolved proteins comprising a desired activity and isolated genes or nucleic acid molecules that encode the evolved proteins. The present invention also provides isolated evolved genes of interest and isolated fusion proteins encoded thereby. The present invention encompasses viruses, non-human cells, in vitro-cultured human cells, and non-human organisms comprising any or more of such genes or proteins produced by the methods of the present invention. Such non-human cells include, but are not limited to, bacterial cells, fungal cells, plant cells, and non-human animal cells.

The present invention additionally provides systems for the directed evolution of macromolecules comprising: (a) a host cell or a population thereof, wherein the host cell comprises a controlling gene encoding a controlling gene product that is required for replication, or enhances the replication of an infective virus, but is not required for the replication of the host cell; and (b) an infective virus according to (a) or a population thereof, wherein the infective virus comprises a complete wild-type virus genome and a gene of interest encoding a fusion protein comprising a protein of interest to be evolved to comprise a desired activity operably linked to an RNA polymerase, and wherein the controlling gene only expresses the controlling gene product in the presence of the desired activity. The systems for the directed evolution of macromolecules can, if desired, further comprise one or more of the following components: a vessel, a cellstat, a growth medium suitable for propagation of the host cells and/or infective viruses, or any other component that is used in the methods of the directed evolution of macromolecules of the present invention that is described elsewhere herein.

The present invention involves the construction of various genes or nucleic acid molecules and proteins comprising two or more elements that are operably linked. As used herein, "operably linked" is intended to mean a functional linkage between two or more elements. For example, an operable linkage between a polynucleotide and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. Toward this end, adapters or linkers may be employed to join the polynucleotide fragments or other manipulations may be involved to provide for convenient restriction sites, removal of superfluous DNA, removal of restriction sites, or the like.

The present invention further involves the construction of fusion proteins that are polypeptides comprising the fusion of two or more proteins and/protein domains. For example, an operable linkage between a protein ligand and RNA polymerase means that their respective amino acid sequences are joined together, whereby the protein ligand and the RNA polymerase retains their respective activities or functions. Toward this end, spacer or linker peptides may be operably linked between any two amino acid sequences to avoid or overcome, for example, potential steric hindrances in vivo between the two corresponding proteins or protein domains.

In certain embodiments, the methods of the present invention comprise increasing the mutation rate to accelerate the evolution of the gene of interest and the protein encoded thereby. Extremely high, yet controllable, in vivo mutation rates are now possible. This broad-spectrum mutagenesis, with as much as $10^5$ times the basal mutation rate, can be controlled within an individual host cell. The increased number of identical phage progeny produced by individuals exhibiting the desired activity will select for the desired activity.

To provide selective pressure, the medium in the lagoons is replaced with new medium and uninfected host cells at a rate that is long with respect to the replication rate of the infective phages (e.g. M13) but short with respect to the replication rate of E. coli. This prevents mutations from being selected for in the E. coli host. The selective pressure on the infective phages and the evolving gene can be increased by altering the medium/host cell exchange rate to be fast relative to the infective phage replication rate.

It is necessary to produce two clones per generation that infect hosts to produce enough phage to prevent washout of a genotype. Assuming phage production of 100/hour and a lagoon transit time of one hour, a maximum mutation rate of four (4) mutations per genome will avoid washout. The percentage of phage progeny which are exact copies of the parent is given by the Poisson distribution where µ=0 is the expected number of mutations and λ is the mutation rate per virion (mutation rate/base*6.4 kbp/genome). A mutation rate of λ=4 gives a 1.8% probability of zero mutations.

$$P(\mu, \lambda) = e^{-\lambda}\lambda^{\mu} \rightarrow P(0, 4) = e^{-4} = 0.0.18 \qquad 1$$
$$\mu!$$

So the maximum per-base mutation rate that a genome could tolerate and still stay in the lagoon is $4/6400 = 6.25 \times 10\text{E-}4$. Existing mutagenesis expression systems can produce mutation rates up to 10 E5 times the basal mutation rate. The basal rate of *E coli* producing M13 phage is $7.2 \times 10\text{E-}7$, easily covering the required phage mutation crossover rate required to avoid washout. Taking a phage production average of 100/hour for normal M13 infection requires us to have a cloning rate of at least 2%: two faithful copies per infection in order to avoid washout. The previous consideration of high mutation rates would seem to allow slower flow rates, which will lower this minimum fraction.

Non-limiting embodiments of the invention include, for example, the following embodiments.

1. A method of directed evolution of macromolecules, the method comprising:

(a) contacting a population of host cells in a culture medium with a population of infective viruses, wherein the host cells contain a controlling gene encoding a controlling gene product that is required for replication, or enhances the replication of the infective viruses, but is not required for the replication of the host cells, wherein the infective viruses comprise a complete wild-type virus genome and a gene of interest encoding a fusion protein comprising a protein of interest to be evolved to comprise a desired activity operably linked to an RNA polymerase, wherein the controlling gene is only capable of expressing the controlling gene product in the presence of the desired activity;

(b) incubating the populations of host cells and infective viruses of (a) under conditions allowing for the mutation of the gene of interest and replication of infective viruses comprising an evolved gene of interest that encodes a fusion protein comprising the desired activity.

2. The method of embodiment 1, wherein the host cells are suitable host cells for infection, replication, and packaging of the infective virus.

3. The method of embodiment 1 or 2, wherein the host cells comprise a plasmid which contains the controlling gene and wherein the host cells lack a genomic copy of the controlling gene.

4. The method of embodiment for 2, wherein the genome of the host cells comprises the controlling gene.

5. The method of embodiment 4, wherein the regulatory region of the controlling gene has been engineered, whereby the controlling gene is only expressed in the presence of the desired activity.

6. The method of any one of embodiments 1-5, further comprising isolating an evolved gene of interest from the population of infective viruses following step (b), and optionally producing a gene encoding the evolved protein by excising from the evolved gene of interest at least the portion of evolved gene of interest encoding the RNA polymerase, whereby the gene encoding the evolved protein comprise the coding sequence of the evolved protein.

7. The method of any one of embodiments 1-5, further comprising:

(c) replenishing the population of host cells of (b) with fresh host cells not infected with the infective virus.

8. The method of embodiment 7, further comprising isolating an evolved gene of interest from the population of infective viruses following step (c), and optionally producing a gene encoding the evolved protein by excising from the evolved gene of interest at least the portion of evolved gene of interest encoding the RNA polymerase, whereby the gene encoding the evolved protein comprises the coding sequence of the evolved protein.

9. The method of any one of embodiments 1-8, wherein the host cells are bacteria.

10. The method of embodiment 9, wherein the bacteria are *Escherichia coli*.

11. The method of embodiment 10, wherein the controlling gene is expressed from a plasmid in the host cells.

12. The method of embodiment 10 or 11, wherein the controlling gene is trxA.

13. The method of any one of embodiments 10-12, wherein the genome of the host cells does not comprise a gene encoding a functional thioredoxin (trxA).

14. The method of any one of embodiments 10-13, wherein the infective viruses are M13 viruses.

15. The method of any one of embodiments 1-14, wherein the RNA polymerase is capable of transcribing a gene in the host cell.

16. The method of any one of embodiments 1-15, wherein the fusion protein is not capable of transcribing the controlling gene in the host cell in the absence of the desired activity.

17. The method of any one of embodiments 1-16, wherein the part of the fusion protein corresponding to the protein of interest has evolved to comprise the desired activity.

18. A gene encoding an evolved protein, wherein the gene is produced or producible by the method of any one of embodiments 1-17, and wherein the evolved protein comprises the desired activity.

19. An evolved protein encoded by the gene of embodiment 18.

20. A system for the directed evolution of macromolecules, the system comprising:

(a) a population of host cells, wherein the host cells comprise a controlling gene encoding a controlling gene product that is required for replication, or enhances the replication of an infective virus, but is not required for the replication of the host cells; and (b) a population of the infective viruses according to (a), wherein the infective virus comprises a complete wild-type virus genome and a gene of interest encoding a fusion protein comprising a protein of interest to be evolved to comprise a desired activity operably linked to an RNA polymerase, and wherein the controlling gene only expresses the controlling gene product in the presence of the desired activity.

21. The system of embodiment 20, further comprising at least one member selected from the group consisting of a vessel, a cellstat, and a growth medium suitable for propagation of the host cells and/or infective viruses.

22. The system of embodiment 20 or 21, where the host cells are the host cells according to any one of embodiments 1-17 and the infective viruses are the infective viruses according to any one of embodiments 1-17.

Other mechanisms can be employed to allow infective virus replication in response to the desired activity. Any host gene necessary for infective virus replication but not necessary for host cell replication can be utilized as the controlling gene (e.g., one could use the bacteriophage T7 growing in host cells mutant for trxA, cmk, gmhB, or galU (Qimron et al. 2006), or lambda bacteriophage growing in host cell mutants for hflC, hflD, hflK, nusB, dnaJ, manZ, ihfA, ihfB, lamB, mall, cyaA, ybeD, yecR, or yneJ (Maynard et al., 2010) or bacteriophage M13 growing on host cell mutants for trxA, dnaA, dnaB, dnaC, dnaG, dnaE, or rep. The absence of such controlling genes need not totally block infective virus replication as long as they reduce infective virus replication. While the examples of embodiments of the invention disclosed herein relate to host cells that are Escherichia coli and viruses that replicate in E. coli, the methods and systems of the present invention are not limited to such host cells and viruses. Any combination of a host cell and a virus that is capable of infecting and reproducing in the host cell can be employed in the methods and systems of the present invention including both prokaryotic and eukaryotic host cells and viruses capable of infecting and reproducing in the host cells.

An alternative embodiment of the present invention comprises replacing the origin of replication in the virus with one that would require a different suite of host enzymes that might be more easily used as controlling genes.

The following examples is offered by way of illustration and not by way of limitation.

EXAMPLES

Example 1: Using HG-Selection to Change the Recognition of the T7 RNA Polymerase The directed evolution methods of the present invention which are referred to as HG-Selection are used to change the specificity of the T7 RNA polymerase from the T7 promoter to a T3 promoter. M13 bacteriophage requires the E. coli protein thioredoxin (trxA) to replicate but E. coli does not require that protein to replicate. Therefore, trxA expression can be used as the basis of the selection aspect of the directed evolution methods of present invention. The host cell (E. coli strain JW5856-2) on which the mutagenized M13 phage are grown contains a point mutation that inactivates the trxA gene. Hence wild type M13 cannot grow on this cell line.

Figure 2:
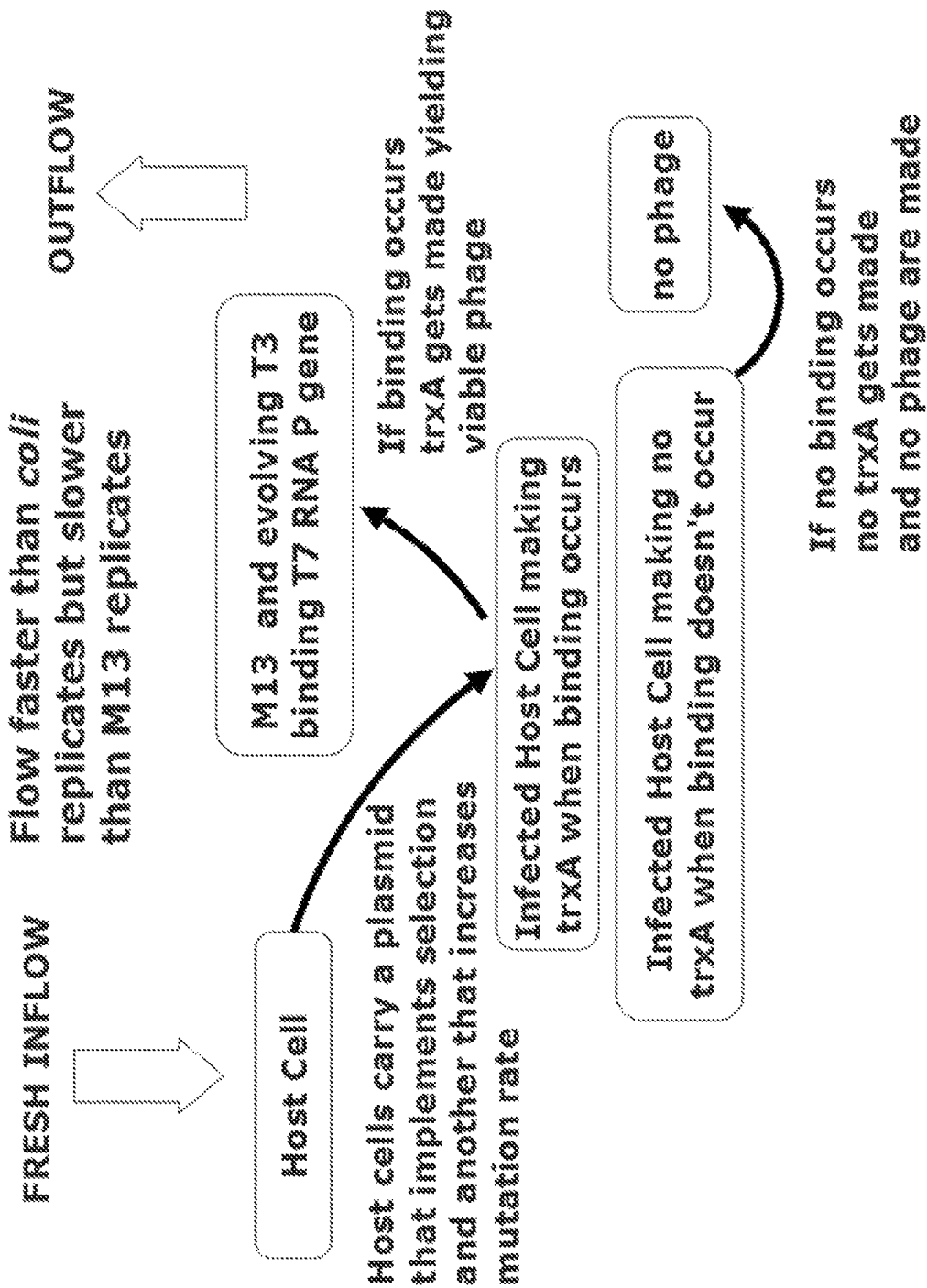
FIG. 2 is a general schematic of Continuous Laboratory Evolution as further described in Example land is a method for evolving a protein like an RNAP to recognize a new sequence.
Figure 5:
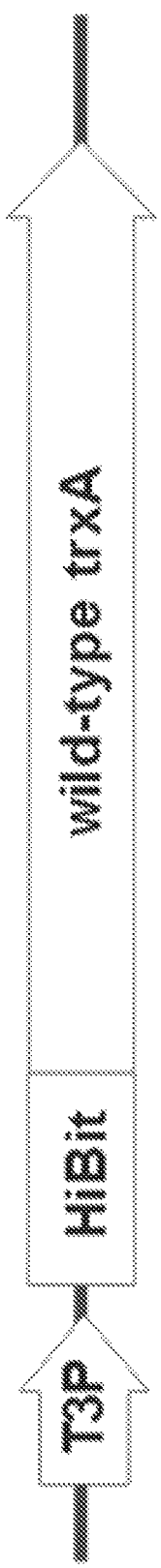
FIG. 5 is a linear diagram of the circular plasmid for expressing HiBit peptide-trxA fusion protein under control of the T3 promoter.

An apparatus is set up comprising the host cells and M13 page according to the scheme set forth in FIG. 2. A selection system (HG-Selection) is installed in the trxA minus host cells. The host cells comprise a selection plasmid comprising a T3 promoter operably linked to wild-type trxA (FIG. 5). When the ligand (T7 RNA polymerase) evolves to recognize the T3 promoter, the operably linked trxA is expressed resulting in the production trxA, and phage can replicate in the host cells.

Example 2: M13 Phage are Incapable of Growing on E. coli that are Defective in trxA To demonstrate that the trxA-based selection system described in Example 1 can be used in the methods of the present invention, M13 phages were grown on the E. coli strains that known to be defective in trxA (A307 and JW5856-2). No phages made plaques were observed when approximately $10^9$ wild-type M13 were plated out on an E. coli trxA minus host JW5856-2 (data not shown). This results indicates the M13 requirement for trxA is not easy to lose.

Figure 3:
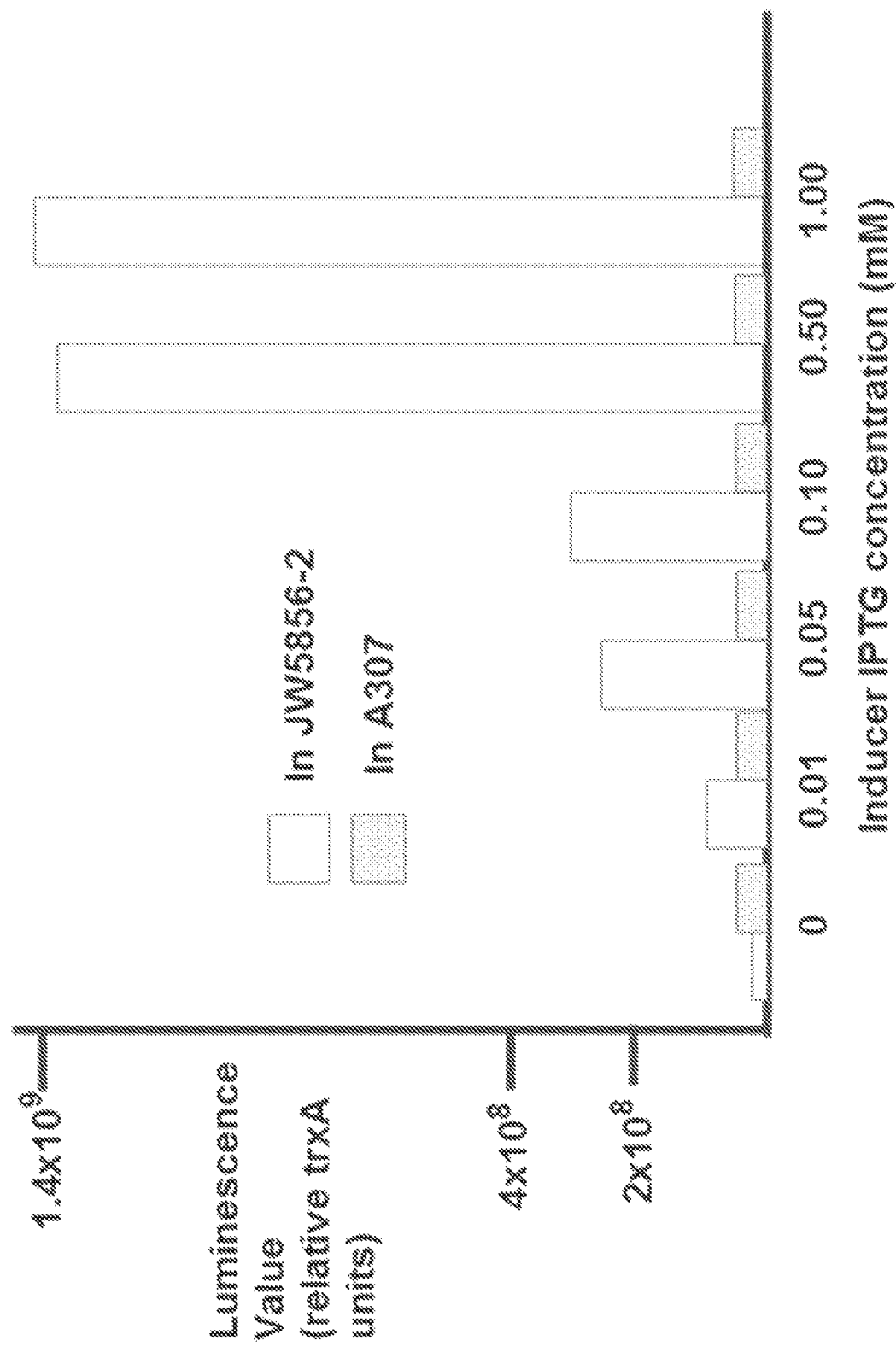
FIG. 3 is a graphical representation of trxA production at concentrations of isopropyl β-D-1-thiogalactopyranoside (IPTG) for *E. coli* trxA minus strains JW5856-2 and A307 as described in Example 2 below.

The best growth was obtained using the E. coli trxA minus strain, JW5856-2 (FIG. 3). The unfilled bars in FIG. 3 represent trxA production from a plasmid where trxA is driven by the tac promoter in JW5856-2. The filled bars in FIG. 3 represent trxA production in E. coli trxA minus strain, A307, a deletion mutation of trxA.

However, the trxA defect in JW5856-2 is due to a point mutation in the trxA gene. Hence it might be possible for that mutation to revert over the long period of a laboratory directed evolution run. JW5856-2 was grown for 7 days under optimal growth conditions (37° C., with antibiotics) for laboratory evolution. To test for reversion, M13 was grown on the surviving cells. No M13 replication was observed, indicating that there were no JW5856-2 revertants in the population of cells capable of supporting the replication of M13.

Example 3: E. coli and M13 Strains

Figure 4:
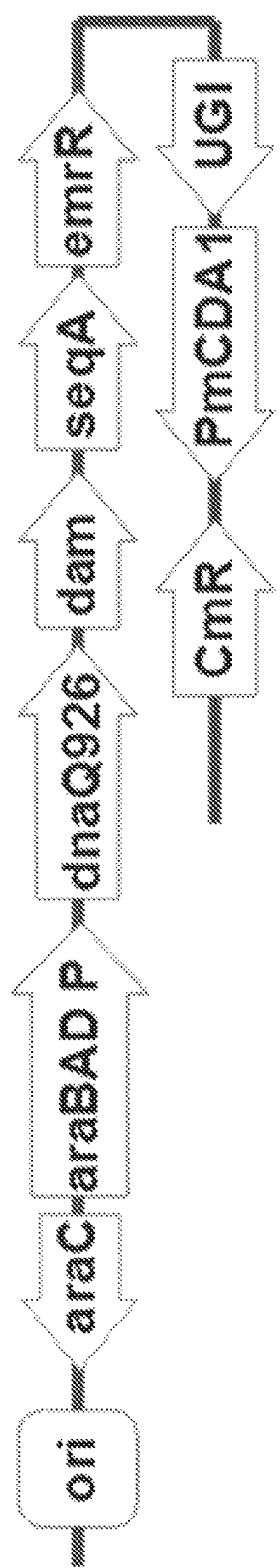
FIG. 4 is a linear diagram of the circular MP6 plasmid.
Figure 6:
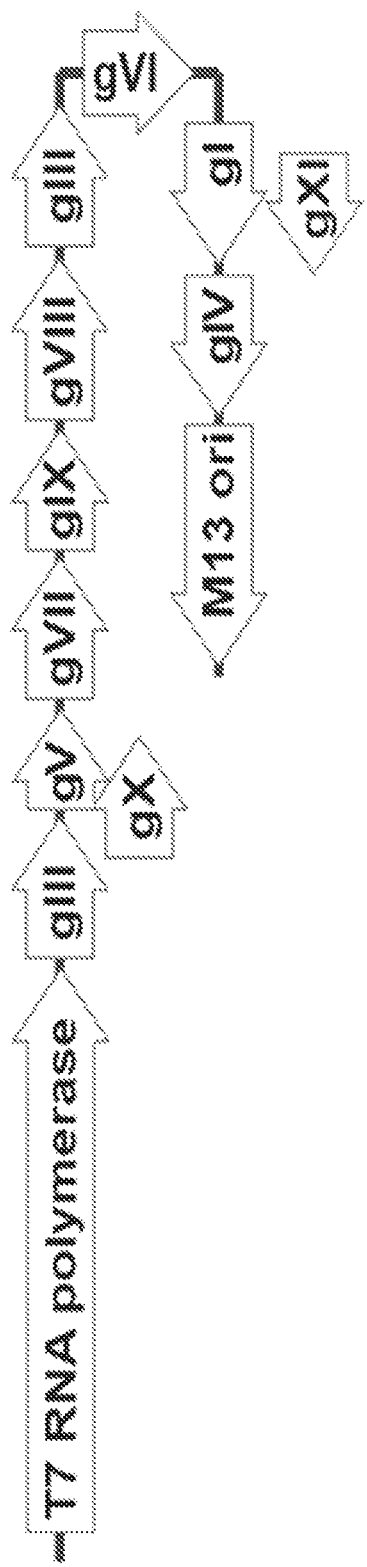
FIG. 6 is a general schematic of the M13 genome with the addition of a gene encoding the wild-type T7 RNA polymerase.

To support the laboratory directed evolution experiment described in Example 1, the following strains have been constructed.
(1) E. coli strain JW5856-2 carrying the MP6 plasmid that elevates the mutation rate approximately 100,000 fold. A linear diagram of the circular MP6 plasmid is provided in FIG. 4.
(2) E. coli strain JW5856-2 carrying both MP6 and a plasmid that expresses wild-type trxA driven by the T3 promoter. The HiBiT Lytic Detection System (Promega Corporation, Madison, Wis.) can be used to track the amount of trxA made via luminescence. A linear diagram of the circular plasmid for expressing HiBit peptide-trxA fusion protein is provided in FIG. 5.
(3) Phage M13 carrying the wild-type T7 RNA polymerase. A linear diagram of the circular genome of this engineered phage is provided in FIG. 6.

Figure 7:
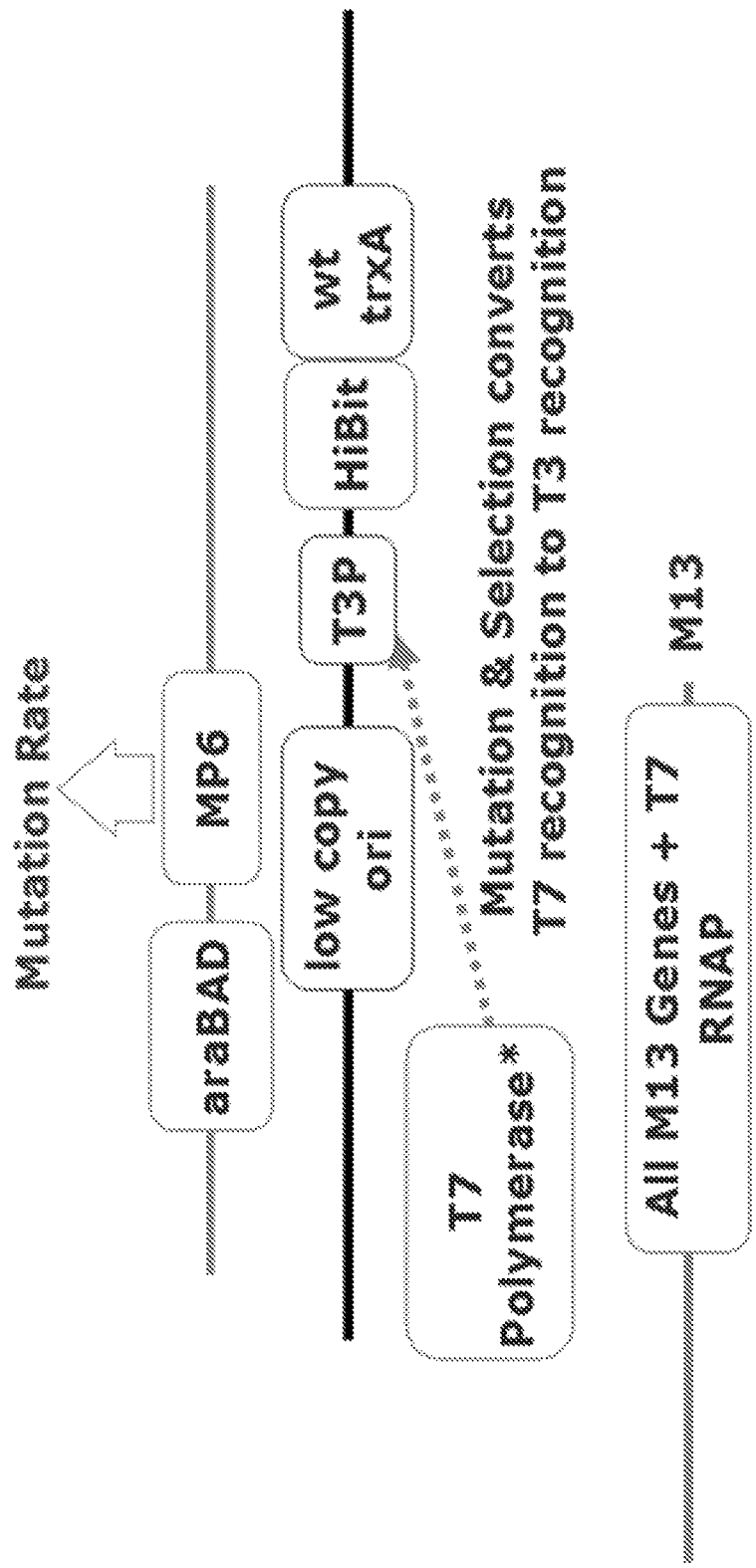
FIG. 7 is a general schematic of the HG-Selection method for changing the promoter recognition/binding of T7 RNA polymerase from recognition binding of the T7 promoter to recognition of the T3 promoter using the *E. coli* gene, trxA, as an example for the controlling gene and the *E. coli* trxA minus strain JW5856-2 harboring the MP6 plasmid to increase the rate of mutagenesis. Additional details are provided in Example 4 below.

Example 4: Evolving the Promoter Binding Activity of T7 RNA Polymerase to Bind to the T3 Promoter As described in Example 1, HG-Selection can be employed to evolve the binding activity of specificity of the T7 RNA polymerase to bind to the T3 promoter. Wild-type T7 RNA polymerase does not recognize the T3 promoter. FIG. 7 is schematic representation of a preferred embodiment of the present invention that is used to evolve the binding activity of specificity of the T7 RNA polymerase to bind to the T3 promoter.

The host cells are the E. coli trxA minus strain JW5856-2 comprising both the MP6 plasmid (FIG. 4) and the plasmid expressing wild-type trxA with HiBit peptide fused to trxA and driven by the T3 promoter (FIG. 5). The fusion of the HiBit peptide to trxA allows for a very sensitive assay for the amount of trxA produced by the host cells. As successful evolution proceeds the amount of luminescence (trxA) should increase The host cells are infected at a multiplicity of approximately 1 with M13 phages carrying the wild-type T7 RNA polymerase (FIG. 6) that have that have been mutagenized separately. The objective of this step is to present the host cells with a phage population containing at least all single mutations in the T7 RNA polymerase as well as many of the double mutants. In this fashion, it is expected that there will be a few phages containing a mutagenized polymerase which will recognize the T3 promoter at least weakly and hence will make some wild-type trxA allowing a low level of phage production to start the process of evolution. The combination of host cells and phages are incubated for about 1.5 hours in the presence of 20 mM arabinose which induces MP6 to elevate the mutation rate. Selection is then applied. From a vessel (lagoon) containing the phages and host cells a half volume of cells plus phages is sent to waste every half hour and one half volume of new host cells is introduced into the lagoon. The replacement host cells and phages with new host cells is repeated every half hour for several or more days, preferably about 2 to about 14 days, more preferably about 4 to about 10 days.

It is expected that phages that carry a T7 RNA polymerase that do not recognize the T3 promoter will not produce progeny and hence will be washed out of the lagoon leaving behind only those phages that carry a mutagenized T7 polymerase that recognizes or binds to the T3 promoter. As time goes on this system will select for variants of the T7 RNA polymerase that bind better and better to the T3 promoter and hence makes more and more trxA and hence more phages per infected cell per hour.

Phage samples from the run on the JW5856-2 host carrying the plasmid expressing wild-type trxA under direction of the T3 promoter are plated out periodically and assayed for their ability to bind to the T3 promoter. DNA is isolated from these mutagenized M13 and sequenced and compared to the sequences of mutant T7 RNA polymerase genes that are known to bind to the T3 promoter.

REFERENCES

Joung, J. K., Ramm, E. I., and Pabo, C. O. A bacterial two-hybrid selection system for studying protein-dna and protein-protein interactions. *PNAS* (97) 7382-7387 (2000).

Quimron, U., Marintchjeva, B., Tabor, S., Richardson, C. Genomewide screens for *Escherichia coli* genes affecting growth of T7 bacteriophage. *PNAS* (103) 19039-19044 (2006).

Manynard, N. D., Birch, E. W., Sanghvi, J. C., Chen, L., Gutschow, M. V., and Covert, M. W. A forward-genetic screen and dynamic analysis of lambda phage host-dependencies revels an extensive interaction network and a new anti-viral strategy. *PLos Genetics* (6) 1-15 (2010).

Russel, M. and Model, P. The role of thioredoxin in filamentous phage assembly. *J. Biol. Chem.* (261) 14997-15005 (1986).

Saluja, D. and Godon, N. Biochemical characterization of *Escherichia coli* temperature-sensitive dnaB mutants, dnaB522, dnaB70, dnaB43, and dnaB *J. Bact* (177) 1. 104-1111 (1995).

Ray, D. S., Dueber, J., and Suggs, S. Replication of Bacteriophage M13 IX. Requirement of the *Escherichia coli* dnaG function for M13 duplex DNA replication. *J. Virology* (16) 348-355 (1975).

Gilchrist, C. A. and Denhardt, D. T. *Escherichia coli* rep gene: sequence of the gene, the encoded helicase, and its homology with uvrD. *Nuc. Acids Res.* (15) 465-475 (1987).

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means "40% or less than 40%. When, in this specification, a range is given as "(a first number) to (a second number)" or "(a first number)–(a second number)," this means a range whose limits include both numbers. For example, "25 to 100" means a range whose lower limit is 25 and upper limit is 100, and includes both 25 and 100.

All publications, patents, and patent applications mentioned in the specification are indicative of the level of those skilled in the art to which this invention pertains. All publications, patents, and patent applications are herein incorporated by reference to the same extent as if each individual publication, patent, or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of directed evolution of macromolecules, the method comprising:
   (a) contacting a population of host cells in a culture medium with a population of infective viruses,
   wherein the host cells are bacteria, wherein the bacteria are *Escherichia coli*, wherein the infective viruses are M13 viruses, wherein the host cells are suitable host cells for infection, replication, and packaging of the infective virus
   wherein the host cells contain a controlling gene encoding a controlling gene product that is required for replication, or enhances the replication of the infective viruses, but is not required for the replication of the host cells,
   wherein the controlling gene is expressed from a plasmid in the host cells, wherein the controlling gene is thioredoxin A (trxA), wherein the genome of the host cells does not comprise a gene encoding a functional trxA,
   wherein the infective viruses comprise a complete wild-type virus genome and a gene of interest encoding a fusion protein comprising a protein of interest to be evolved to comprise a desired activity operably linked to an RNA polymerase, wherein the controlling gene is only capable of expressing the controlling gene product in the presence of the desired activity;
   (b) incubating the populations of host cells and infective viruses of (a) under conditions allowing for the mutation of the gene of interest and replication of infective viruses comprising an evolved gene of interest that encodes a fusion protein comprising the desired activity.

2. The method of claim 1, further comprising isolating an evolved gene of interest from the population of infective viruses following step (b), and optionally producing a gene encoding the evolved protein by excising from the evolved gene of interest at least the portion of evolved gene of interest encoding the RNA polymerase, whereby the gene encoding the evolved protein comprise the coding sequence of the evolved protein.

3. The method of claim 1, further comprising:
   (c) replenishing the population of host cells of (b) with fresh host cells not infected with the infective virus.

4. The method of claim 3, further comprising isolating an evolved gene of interest from the population of infective viruses following step (c), and optionally producing a gene encoding the evolved protein by excising from the evolved gene of interest at least the portion of evolved gene of interest encoding the RNA polymerase, whereby the gene encoding the evolved protein comprises the coding sequence of the evolved protein.

5. The method of claim 1, wherein the RNA polymerase is capable of transcribing a gene in the host cell.

6. The method of claim 5, wherein the fusion protein is not capable of transcribing the controlling gene in the host cell in the absence of the desired activity.

7. The method of claim 1, wherein the part of the fusion protein corresponding to the protein of interest has evolved to comprise the desired activity.

\* \* \* \* \*